US010782271B2

(12) United States Patent
Smith, III

(10) Patent No.: US 10,782,271 B2
(45) Date of Patent: Sep. 22, 2020

(54) SYNTHETIC CANNABINOID STRUCTURE CLASSIFICATION USING THE BRIDGE CARBONYL FREQUENCY IN VAPOR PHASE

(71) Applicant: Lewis Wayne Smith, III, Bridgeton, NJ (US)

(72) Inventor: Lewis Wayne Smith, III, Bridgeton, NJ (US)

( * ) Notice: Subject to any disclaimer, the term of this patent is extended or adjusted under 35 U.S.C. 154(b) by 0 days.

(21) Appl. No.: 16/350,805

(22) Filed: Jan. 14, 2019

(65) Prior Publication Data
US 2019/0178858 A1    Jun. 13, 2019

Related U.S. Application Data

(60) Provisional application No. 62/709,346, filed on Jan. 17, 2018.

(51) Int. Cl.
| | |
|---|---|
| *G01N 30/88* | (2006.01) |
| *G01N 30/86* | (2006.01) |
| *G01N 33/94* | (2006.01) |
| *G16C 20/20* | (2019.01) |
| *G01N 30/02* | (2006.01) |
| *G01N 30/74* | (2006.01) |

(52) U.S. Cl.
CPC ..... *G01N 30/8682* (2013.01); *G01N 30/8631* (2013.01); *G01N 30/8696* (2013.01); *G01N 30/88* (2013.01); *G01N 33/948* (2013.01); *G16C 20/20* (2019.02); *G01N 30/74* (2013.01); *G01N 2030/025* (2013.01); *G01N 2030/743* (2013.01); *G01N 2030/884* (2013.01)

(58) Field of Classification Search
CPC .......... G01N 30/8696; G01N 30/8631; G01N 30/74; G01N 2030/743; G01N 2030/025; G01N 2030/884
USPC ................................. 250/281, 282
See application file for complete search history.

(56) References Cited

U.S. PATENT DOCUMENTS

2018/0143212 A1* 5/2018 Giese ................. B01D 11/0288

* cited by examiner

*Primary Examiner* — Michael Maskell

(57) ABSTRACT

Synthetic Cannabinoids are the most complex branch of designer drugs encountered in forensic chemistry. A screening method has been developed that can accurately identify the correct structural category of an unknown Synthetic Cannabinoid. Knowledge of this information is very important when no reference data or standards are available since certain sub-categories contain Schedule I Controlled Dangerous Substances. The Bridge portion of these molecules present a unique carbonyl band cluster within a small 200 wavenumber interval of the mid-infrared region that can only exist in vapor phase through GC/FTIR light-pipe technology or heated static vapor cell FTIR. This special relationship is not applicable to any other forms of solid phase vibrational spectroscopy (FTIR, RAMAN) including GC/FTIR solid-deposit techniques. The carbonyl frequency from the Bridge is used as the first step in the screening process which separates the entire forensically encountered class of Synthetic Cannabinoids into 35 sub-categories. Additional bands within the cluster from secondary functional groups, rotational isomerism, and fermi resonance add further refinement within these categories.

3 Claims, 6 Drawing Sheets

BRIDGE TABLE

| BRIDGE C=O | BRIDGE FUNCTIONAL GROUP | Additional C=O FROM PIECE | UNIQUE C=O | Adjoining Pieces |
|---|---|---|---|---|
| 1753 | ESTER | | 1779-1780 | INDAZOLE / QUINOLINE |
| 1747 to 1751 | ESTER | | | INDOLE / Quinoline or Isoquinoline |
| 1749 to 1750 | ESTER | | | INDOLE / NAPHTHALENE |
| 1747 to 1749 | ESTER | | 1777-1778 | INDAZOLE / NAPHTHALENE |
| 1734 | ESTER | 1759 | | INDAZOLE / ESTER |
| 1718 | ESTER | | 1747 | INDAZOLE / ADAMANTYL |
| 1707 | SECONDARY AMIDE | | | INDAZOLE / NAPHTHALENE |
| 1703 | SECONDARY AMIDE | | | Tetrahydrobenzo[b]thieno / NAPHTHALENE |
| 1696 to 1698 | SECONDARY AMIDE | | | INDOLE / NAPHTHALENE |
| 1697 | SECONDARY AMIDE | | | INDAZOLE / QUINOLINE |
| 1696 | SECONDARY AMIDE | | | INDAZOLE / 1-Methyl-Phenylethyl |
| 1695 to 1697 | SECONDARY AMIDE | 1752-1757 | | INDAZOLE / ESTER |
| 1691 to 1692 | SECONDARY AMIDE | | | INDAZOLE / ADAMANTYL |
| 1690 | SECONDARY AMIDE | | | INDOLE / QUINOLINE |
| 1685 to 1688 | SECONDARY AMIDE | 1684-1688 | | INDAZOLE / PRIMARY AMIDE |
| 1685 to 1686 | SECONDARY AMIDE | | | INDOLE / BENZYL |
| 1685 to 1686 | SECONDARY AMIDE | 1752-1753 | | INDOLE / ESTER |
| 1685 | SECONDARY AMIDE | | | INDOLE / Methyl-CYCLOPROPYL |
| 1681 to 1682 | SECONDARY AMIDE | | | INDOLE / ADAMANTYL |
| 1680 | SECONDARY AMIDE | | | INDOLE / Bicyclo[2.2.1]hept-2-yl |
| 1677 | METHANONE | | | INDAZOLE / CYCOPROPYL |
| 1673 | METHANONE | | | CARBAZOLE / NAPHTHALENE |
| 1671 to 1672 | ETHANONE | | | INDOLE / BENZENE |
| 1671 | METHANONE | | | INDAZOLE / NAPHTHALENE |
| 1668 to 1671 | SECONDARY AMIDE | 1721-1723 | 1831-1834 | INDOLE / PRIMARY AMIDE |
| 1668 to 1670 | ETHANONE | | | INDOLE / NAPHTHALENE |
| 1668 to 1669 | METHANONE | | | BENZIMIDAZOLE / NAPHTHALENE |
| 1666 to 1667 | METHANONE | | | PYRROLE / NAPHTHALENE |
| 1662 to 1663 | METHANONE | | | INDOLE / CYCLOPROPYL |
| 1661 | METHANONE | | | INDOLE / BENZENE |
| 1661 | SECONDARY AMIDE | | | Imidazo[1,2-c]quinazoline / 3-PYRIDINE |
| 1659 | METHANONE | | | INDOLE / PIPERAZINE |
| 1654 to 1657 | METHANONE | | | INDOLE / NAPHTHALENE |
| 1654 | METHANONE | | | INDOLE / ADAMANTYL |
| 1646 | METHANONE | | | 2-Methyl-INDOLE / NAPHTHALENE or 2'-PYRROLE/NAPHTHALENE |

FIGURE 1. - *BRIDGE TABLE*

| BRIDGE C=O | BRIDGE FUNCTIONAL GROUP | Additional C=O FROM PIECE | UNIQUE C=O | Adjoining Pieces |
|---|---|---|---|---|
| 1753 | ESTER | | 1779-1780 | INDAZOLE / QUINOLINE |
| 1747 to 1751 | ESTER | | | INDOLE / Quinoline or Isoquinoline |
| 1749 to 1750 | ESTER | | | INDOLE / NAPHTHALENE |
| 1747 to 1749 | ESTER | | 1777-1778 | INDAZOLE / NAPHTHALENE |
| 1734 | ESTER | 1759 | | INDAZOLE / ESTER |
| 1718 | ESTER | | 1747 | INDAZOLE / ADAMANTYL |
| 1707 | SECONDARY AMIDE | | | INDAZOLE / NAPHTHALENE |
| 1703 | SECONDARY AMIDE | | | Tetrahydrobenzo[b]thieno / NAPHTHALENE |
| 1696 to 1698 | SECONDARY AMIDE | | | INDOLE / NAPHTHALENE |
| 1697 | SECONDARY AMIDE | | | INDAZOLE / QUINOLINE |
| 1696 | SECONDARY AMIDE | | | INDAZOLE / 1-Methyl-Phenylethyl |
| 1695 to 1697 | SECONDARY AMIDE | 1752-1757 | | INDAZOLE / ESTER |
| 1691 to 1692 | SECONDARY AMIDE | | | INDAZOLE / ADAMANTYL |
| 1690 | SECONDARY AMIDE | | | INDOLE / QUINOLINE |
| 1685 to 1688 | SECONDARY AMIDE | 1684-1688 | | INDAZOLE / PRIMARY AMIDE |
| 1685 to 1686 | SECONDARY AMIDE | | | INDOLE / BENZYL |
| 1685 to 1686 | SECONDARY AMIDE | 1752-1753 | | INDOLE / ESTER |
| 1685 | SECONDARY AMIDE | | | INDOLE / Methyl-CYCLOPROPYL |
| 1681 to 1682 | SECONDARY AMIDE | | | INDOLE / ADAMANTYL |
| 1680 | SECONDARY AMIDE | | | INDOLE / Bicyclo[2.2.1]hept-2-yl |
| 1677 | METHANONE | | | INDAZOLE / CYCOPROPYL |
| 1673 | METHANONE | | | CARBAZOLE / NAPHTHALENE |
| 1671 to 1672 | ETHANONE | | | INDOLE / BENZENE |
| 1671 | METHANONE | | | INDAZOLE / NAPHTHALENE |
| 1668 to 1671 | SECONDARY AMIDE | 1721-1723 | 1831-1834 | INDOLE / PRIMARY AMIDE |
| 1668 to 1670 | ETHANONE | | | INDOLE / NAPHTHALENE |
| 1668 to 1669 | METHANONE | | | BENZIMIDAZOLE / NAPHTHALENE |
| 1666 to 1667 | METHANONE | | | PYRROLE / NAPHTHALENE |
| 1662 to 1663 | METHANONE | | | INDOLE / CYCLOPROPYL |
| 1661 | METHANONE | | | INDOLE / BENZENE |
| 1661 | SECONDARY AMIDE | | | Imidazo[1,2-c]quinazoline / 3-PYRIDINE |
| 1659 | METHANONE | | | INDOLE / PIPERAZINE |
| 1654 to 1657 | METHANONE | | | INDOLE / NAPHTHALENE |
| 1654 | METHANONE | | | INDOLE / ADAMANTYL |
| 1646 | METHANONE | | | 2-Methyl-INDOLE / NAPHTHALENE or 2'-PYRROLE/NAPHTHALENE |

CLASSIFICATION INTO THREE PIECES
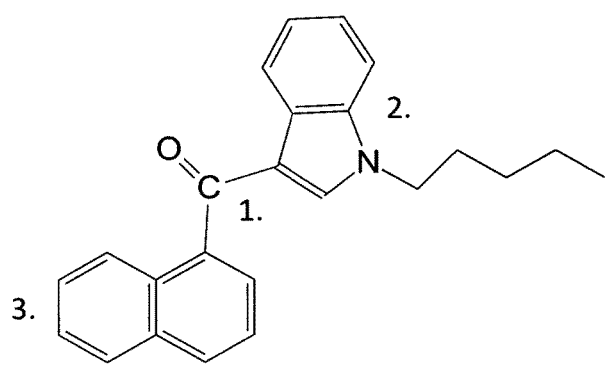
WITH SECONDARY RING
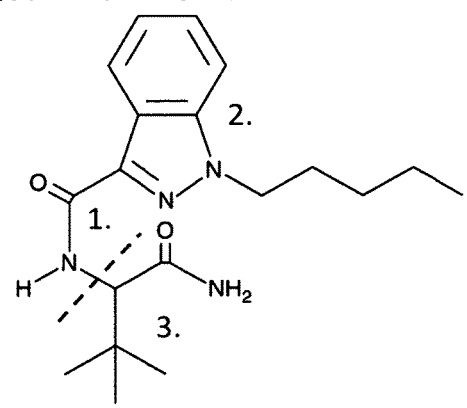
*WITH SECONDARY FUNCTIONAL GROUP
1. BRIDGE
2. CORE RING SYSTEM
3. SECONDARY RING SYSTEM OR *FUNCTIONAL GROUP
FIGURE 6.

SYNTHETIC CANNABINOID STRUCTURE CLASSIFICATION USING THE BRIDGE CARBONYL FREQUENCY IN VAPOR PHASE

BACKGROUND OF THE INVENTION

This invention involves the mid-infrared spectral examination of just one specific site from the molecular framework of Synthetic Cannabinoids in order to quickly identify its proper class variety. Infrared Spectroscopy is unique to all other instrumental techniques in that the spectrum can drastically change depending on the physical state of the sample (solid, liquid, gas). A unique band cluster has been discovered that can easily classify this complex family of Synthetic Cannabinoids into their perspective sub-categories. This relationship can only exist in vapor (gas) phase and is found within a small 200 wavenumber region of the mid-infrared region from 1646 $cm^{-1}$ to 1834 $cm^{-1}$ and is not applicable with any other infrared technique. Even though varied embodiments of infrared spectroscopy exist, no prior art of vapor phase has been applied to the complete classification of these compounds.

Forensic examination of the majority of seized drug samples involves a solvent dilution followed by Gas Chromatography (GC) due to the limited quantity and/or impurity of the sample. Over the years the "gold label" standard of analyzing the gas effluents from the GC column was by Electron Impact Quadrupole Mass Spectrometry (EIMS). In some cases, the mass spectra produced from this technique results in either no discernable Molecular Ion identity and/or poor fragmentation patterns yielding few ions of significant abundance. Coupling Gas Chromatography with Fourier Transform Infrared Spectrometry (GC/FTIR) has proved useful for this class of designer drugs which have proven to be stable in the vapor phase between 250-290° Centigrade. The only requirement for this invention is that the spectrum of the compound is measured at an elevated temperature sufficient to keep it in the vapor state. The hardware employed to achieve this can either be the gold coated light pipe flow cell from a GC/FTIR system or a heated static vapor cell on a bench-top FTIR system.

Progress in Infrared Vapor Phase Technology has been very slow to evolve due to the limitations imposed by the instruments themselves. Dispersive prism spectrophotometers were not commercially available until 1947. An increase in spectral resolution was achieved by diffraction gratings used in later models. However, both types failed to have scan speeds fast enough to keep up with real-time gas chromatographic effluents. Early GC/IR proto-types did not offer spectra collected in the vapor phase. Infrared spectra were recorded in the condensed phase from various forms of GC column trapping techniques. In 1975 Sadtler Research Labs, Inc. (Philadelphia, Pa.) commercially produced the CIRA 101 GC/IR unit which was the first successful GC column coupled to a heated vapor cell (1). Chromatographic peaks were trapped in the cell and scanned using a stop-flow technique.

The greatest impact to this technology occured with the development of multiplex-scanning interferometric techniques developed by Digilab, Inc. (Cambridge, Mass.) in 1970. Interferometers offered superior scanning speeds over traditional monochrometers and a higher optical throughput for greater sensitivity. With continual fast-scanning FTIR spectrometers, the entire chromatographic run can be stored digitally. This technology was significantly enhanced by Tomas Hirschfeld in 1986 in the development of the Hewlett Packard 5965A GC/IRD unit. Signal noise was greatly reduced by using an interferometer much smaller in comparison to that within a standard bench-top FTIR. Likewise the vapor cell diameter was reduced to 1 mm with matching infrared optics. This has undergone three revisions with the current version today being the IRD-3 from ASAP, Inc. (Covington, Ky.). Despite all of the great advances and refinements of this technology culminating into the creation of the GC/IRD, these units have not seen very wide distribution in the last 30 years resulting in four different owners over the years. Mass Spectrometry via bench-top GC/MS units seems to have dominated the market over GC/IRD despite the fact that it is incapable of distinguishing positional isomers of organic compounds.

D. Welti, from England, was the first author in 1970 to bring to attention the value of vapor phase as a different dimension of infrared data in the book "*Infrared Vapour Spectra*" (2). Over 300 spectra were collected by injecting liquids directly into a heated vapor cell using a dispersive spectrophotometer. Since then, only one other book has followed in 1984 "*The Interpretation of Infrared Vapor Spectra*" (3) by Richard Nyquist of the Dow Chemical Company. This work systematically classifies and interprets spectra from the Sadtler Vapor Phase collection of 9200 spectra. Since this work, nothing has followed dealing with vapor phase spectral interpretation. These aforementioned books do not cover the interpretation of drugs in forensic analysis.

Over the years, there have been only a limited number of reference spectral collections available in the vapor state. There are only 3 sources of commercially available infrared vapor phase search digital libraries. Sadler Research Labs, Inc. (Philadelphia, Pa.) was contracted to perform the first Vapor Phase EPA Collection in 1975. This has resulted in 9200 FTIR vapor phase spectra being collected between the years of 1977 to 1985 (4). Aldrich Chemical Company (Milwaukee, Wis.) collected 6000 vapor phase spectra in 1989 (5). NIST (Gaithersburg, Md.) has completed 2120 vapor spectra using an Hewlett Packard GC/IRD in 1992 (6). Werner Herres in 1987 published a book containing 73 GC/FTIR spectra of terpene like compounds (7). None of these collections cover the new designer drugs synthesized in the last 10 years.

The total combination of these three factors: Limited instrument distribution, lack of education, literature, and the availability of current data have hindered the popularity of vapor phase technology. Hence, no problem solving advances by infrared vapor technology have been applied to new generations of synthetic compounds. This field has been out of vogue long before the synthesis of the first generation of Synthetic Cannabinoids in the early 90's, followed by the surge of their illicit use beginning in 2009 posing new challenges to forensic laboratories for their identification. Therefore, despite the limited progress made in vapor phase spectral interpretation, this invention proves the value of this technique in the ability to filter, by class, the largest and complex group of illicit compounds encountered in Forensic Chemistry.

REFERENCES CITED FOR THE BACKGROUND OF THE INVENTION

1. Shaps, Richard H. and Antonio Varano "*A GC/ir as an accessory for an ir spectrometer*" American Laboratory, November 1975
2. Welti, D. "*Infrared Vapour Spectra*" 1970 Heyden & Sons, Ltd. London ISBN 0-8550-1019-3

3. Nyquist, Richard *"The Interpretation of Vapor-Phase Infrared Spectra—Volume 1 Group Frequency Data"* 1984 Sadtler Research Labs, Phillladelphia Pa. ISBN 0-8456-0092-3
4. Available from BIORAD Informatics Division 2000 Market Street, Philadelphia Pa.
5. Pouchert, Charles *"Aldrich Library of FT-IR Spectra—Vapor Phase Volume 3"* 1989 Aldrich Chemical Company LCCN 84-72539
6. NIST/EPA Gas-Phase Infrared Database JCAMP Format—SRD 35
7. Herres, Werner *"HRGC-FTIR: Capillary Gas Chromatography—Fourier Transform Infrared Spectroscopy"* 1987 Alfred Huthing Verlag Heidelberg ISBN 3-7785-1061-4

SUMMARY OF THE INVENTION

The complex molecular structure found in Synthetic Cannabinoids has resulted in a large number of both sub-class varieties and their derivatives. Forensic laboratories are challenged daily with the problem of continually updating standards and data in order to solve the identity of endless new designer drugs. This invention aids in the quick screening and interpretation of unknown Synthetic Cannabinoid specimens routinely encountered during forensic examinations using Infrared Spectroscopy.

The Bridge Table illustrated in FIG. 1 enables users to quickly find a Synthetic Cannabinoid sub-class by matching all Carbonyl values between 1850-1640 wavenumbers from an unknown spectrum to the closest values listed in the table. All categories of the Synthetic Cannabinoid family were defined in this table molecularly in terms of three basic pieces. The most important piece is the Bridge: the chain (ketone, amide, or ester) containing a Carbonyl group linking the two ring systems together. The first step is to match a value to the first column headed "BRIDGE C=O" which, in most cases, is the strongest band within the cluster. Any additional bands are correlated with columns 3 and 4 headed "ADDITIONAL C=O FROM PIECE" and "UNIQUE C=O". Once the peak values are properly matched, the correct sub-class will be given in columns 2 and 5 which yields the molecular structure in terms of the Bridge and its two adjoining end pieces.

Using the Carbonyl band cluster as a screening method can help quickly identify the correct Synthetic Cannabinoid Class and its legal status. There are certain sub-classes within the table, such as the Naphthoyl Indoles (indolemethanone-naphthalene) which contain derivatives that are Schedule I Controlled Dangerous Substances. Other categories, such as (carbazole-methanone-naphthalene) are non-controlled substances. Moreover, this technique provides an advantage when no standards or data are available for comparison and to warrant the need for further evaluation. This information coupled with other supplemental data can help to properly choose the correct standard for full confirmation. Therefore, this technology can be used in the form of screening software for miniature infrared systems for field use as well as full bench-top and advanced infrared data stations within the laboratory. Additional logic steps may be added to further refine the Tail portion and ring substitution to further narrow derivatives within a sub-category.

The exclusive advantages found within the Carbonyl cluster is a combination of both the complex structural nature of Synthetic Cannabinoids and the infrared properties of molecules in the vapor state. In vapor phase, carbonyl frequency values are a direct function of electron density contributions from neighboring bonded groups. The variety of rings and functional groups attached to the Bridge within these derivatives creates many different and unique electronic enviroments. This results in a carbonyl shift of over 100 wavenumbers which make separation of the sub-classes possible. In the few instances where slight overlapping occurs, the additional extra and/or unique bands within the cluster easily separate the two categories. This unique band cluster exists due to every single Carbonyl band being visually observed and accounted for with no masking of other bands or overlap of one another. These values are reproducible and are not shifted by intermolecular hydrogen bonding or split by differences within the crystal lattice structure. Thus, all Carbonyl bands in the vapor phase are completely resolved and reproducible with no wavenumber shifts.

This invention cannot be applied to any other infrared technique. It can be closely approached by using long pathlength cells and examining the analyte in dilute solution. A solvent must be chosen that does not absorb in the carbonyl region. However due to the large variety of derivatives, not all Synthetic Cannabinoids will be soluble in the same solvent. Other problems exist such as the polar association of solvent/analyte. In addition, the long cell pathlength requires solvent compensation in the reference beam because additional bands will appear from the solvent that are invisible in normal pathlengths of less than 0.5 mm. However, even if all of these obstacles are overcome, the use of different solvents would result in different frequency shifts of the carbonyl absorption due to its association with the solvent. Thus invalidating the entire method as the Bridge frequency defines the subclass and all measurements must reflect changes from the molecule itself, not the polarity of the surrounding medium. This relationship will not work for any solid phase techniques available—ATR (Attenuated Reflectance), DRIFTS (Diffuse Reflection), Transmittance (KBr wafers), MULLS (ground in Fluorolube or Nujol), and Film (dissolved in solvent and evaporated). The aforementioned problems are due to strong molecular self-association through hydrogen bonding of molecules existing in the solid state causing carbonyl bands to have frequency shifts to longer wavelengths and in some cases overlap with each other. Depending upon the molecular structure, different forms of hydrogen bonding within the crystal orientation are possible resulting in polymorphism. Importantly, different polymorphic forms yield different spectra of the same compound.

For example, only vapor phase is capable of resolving both carbonyl bands found within FUBINACA, PINACA, CHMINACA types (indazole-secondary amide-primary amide). This is of particular importance because there are controlled Schedule I CDS derivatives present within this group. This class, encompassing a large number of derivatives, contains two Amide functional groups within the same molecule displaying two Carbonyl bands (primary Amide I and secondary Amide I) in the vapor phase. The separation of these two bands cannot be accomplished using solid phase FTIR methods due to the strong self-association of intermolecular Hydrogen Bonding. Separation is also not possible using GC/FTIR direct deposit solid phase techniques of DiscovIR-GC (Spectra Analysis Marlborough, Mass.) because the sample, which is in the vapor state during elution from the GC column, is cooled and condensed to a solid state before the spectrum is acquired. In this case, the results were even poorer than ATR because the column effluent is plated onto the substrate as an "amorphous film" resulting in a loss band sharpness and definition. FIG. 2 illustrates the ability of vapor phase to separate the carbonyl bands of 5-fluoro AB-PINACA in comparison to other infrared methods. In vapor phase (the bottom spectrum) clearly shows that there are only two carbonyl bands 1726 cm$^{-1}$ for the primary amide I band and 1688 cm$^{-1}$ for the secondary amide I band (Bridge Carbonyl). The unique aspect of this invention is that every single individual carbonyl within the molecule is observed, identified, and classified with no influences from the outside enviroment.

Additional carbonyl bands from other functional groups present, "ADDITIONAL C═O FROM PIECE", add further refinement in identifying a sub-category. The maximum number of bands possible in the cluster is three. Examples of this type are from the class indole-secondary amide-primary amide. Although there are only two bands arising from the primary and secondary amide functional groups, a third unique band arises from fermi resonance from 1831-1834 wavenumbers. Bands of this type are listed in the "UNIQUE C═O" column. Synthetic Cannabinoids containing an Ester Bridge linked to a indazole core ring have displayed two carbonyl bands in the case where there is only one carbonyl group present within the molecule. In vapor phase molecules freely rotate and vibrate unhindered in space. In special cases, bond rotation can also occur within a molecule causing rotational isomers to exist. FIG. 3 illustrates the special case of APINAC from the indazole-ester-adamantyl class. An additional higher frequency (shift to shorter wavelengths) carbonyl band is created from the conformer in which the bridge carbonyl is in close vicinity of the unpaired electron pair of Nitrogen in position 2 on the indazole ring. This carbonyl frequency shift, from 25-30 cm$^{-1}$, is a result of the "Field Effect". That does not exist within solid phase vibrational spectroscopic methods (i.e. FTIR and FT-Raman) as bond rotation cannot occur within the rigid crystal network of solids or the liquid state in which the molecules are completely next to each other. Further proof of this can be found in FIG. 4. By replacing the core ring indazole with indole, this additional band disappears because Nitrogen is not present in position 2 of the indole ring.

This data has proven vapor phase FTIR has the ability to resolve all carbonyl bands that are obscured in the solid phase by hydrogen bonding. This is also applicable to some examples within the Naphthoylindole series which are highly crystalline in nature. This class (indole-methanone-naphthalene) has only one ketone carbonyl and no other polar functional groups, so molecular self-association is minimal. Even in this case, vapor phase will still shift the carbonyl frequency to a higher frequency. This is an advantage because it is moving away from the highly occupied fingerprint region towards the middle of the spectrum where no other bands reside. FIG. 5 illustrates two examples of JWH-081 and its 5-methoxynaphthyl isomer which have nuances in the crystalline state making the carbonyl hard to identify. Normally, in the solid state, the carbonyl band is the strongest band in the entire spectrum with the C═C ring stretching bands (Wilson [8a], [8b]) being relatively weak. In the case of these two examples, the Bridge Carbonyl (marked with an asterisk*on the tip) is fused to the left hand side of the aromatic ring band [8a]. The intensity of the carbonyl band is also weaker than the aromatic ring stretching bands which is an anomaly within this class. In the vapor phase, however, both of these challenges are easily overcome: the methanone bridge carbonyl band is shifted away from the aromatic ring stretching bands and its intensity is enhanced significantly. For JWH-081 5-methoxynaphthyl isomer, the carbonyl which was one of the weakest bands in the solid phase spectrum is now the strongest band in the entire spectrum for vapor phase. Vapor phase has proven to be extremely valuable in clearly identifying all carbonyl band present in every Synthetic Cannabinoid example making the Bridge Table presented in this invention possible.

BRIEF DESCRIPTION OF THE DRAWINGS

FIG. 1. is a table linking all carbonyl absorption band frequencies in tabular format directly to the Synthetic Cannabinoid Categories in terms of three basic structural pieces recognizing that the implementation of these categories is the functional equivalent of indexed spectral matching analysis.

FIG. 6. is a molecular structural diagram explaining the rules and nomenclature for dividing all Synthetic Cannabinoid categories into three basic pieces. The ring systems and functional groups present in each piece are directly linked to the infrared tabular data resulting in a basis for the identification of any unknown Synthetic Cannabinoid in terms of a basic molecular structure.

DESCRIPTION OF THE INVENTION

Figure 2:
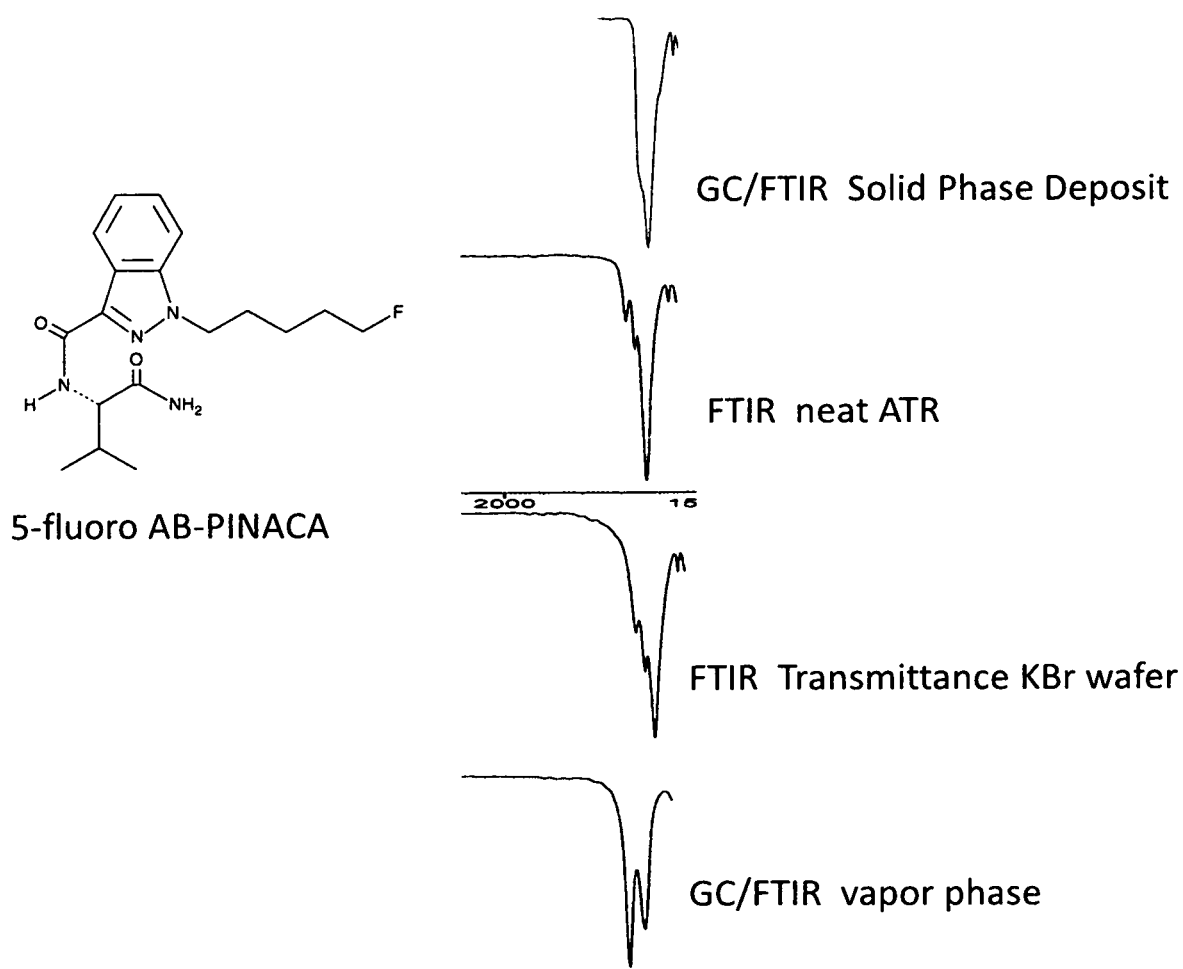
FIG. 2. is the overlay of four infrared spectral plots of 5-fluoro AB-PINACA in the 1650 wavenumber region illustrating that vapor phase is the only infrared technique capable of resolving and identifying both carbonyl bands from this molecule.
Figure 3:
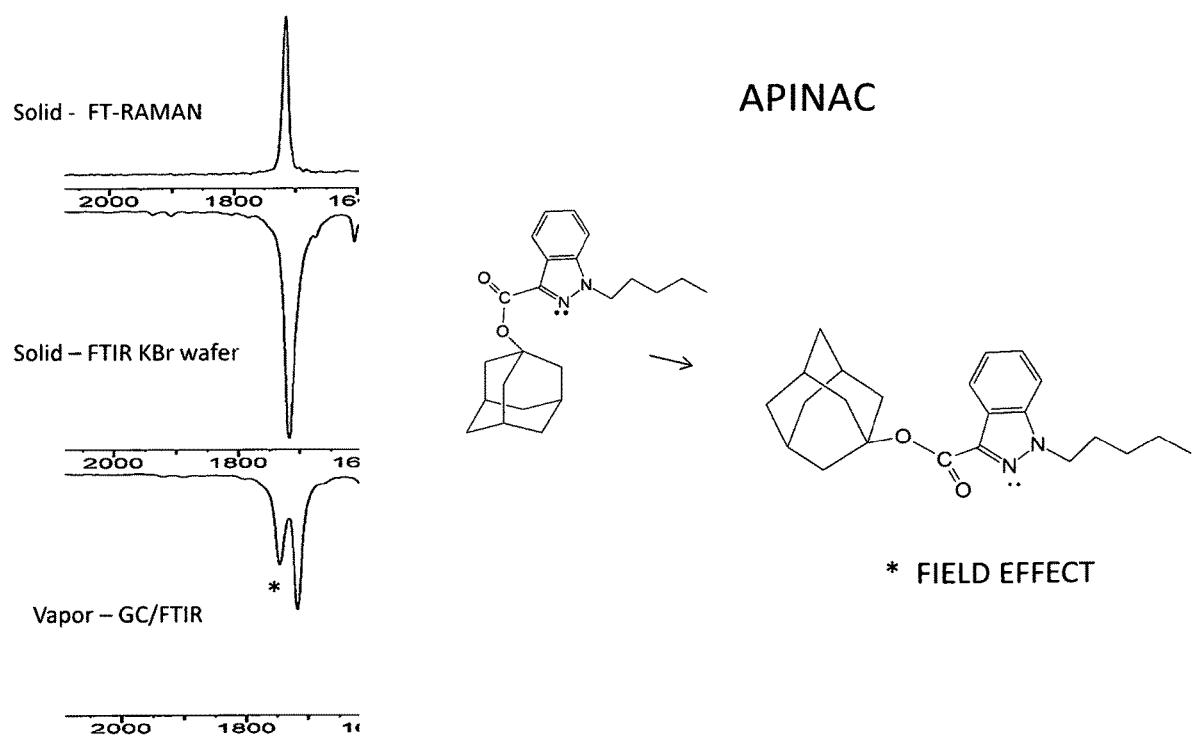
FIG. 3. is the overlay of three spectral plots of APINAC in the 1750 wavenumber region. Molecular rotation of this molecule is only possible in the vapor phase causing a Field Effect resulting in an additional carbonyl band as shown in the bottom spectrum. This does not occur in any form of solid phase vibrational spectroscopy all of which lead to only one single carbonyl absorption.
Figure 4:
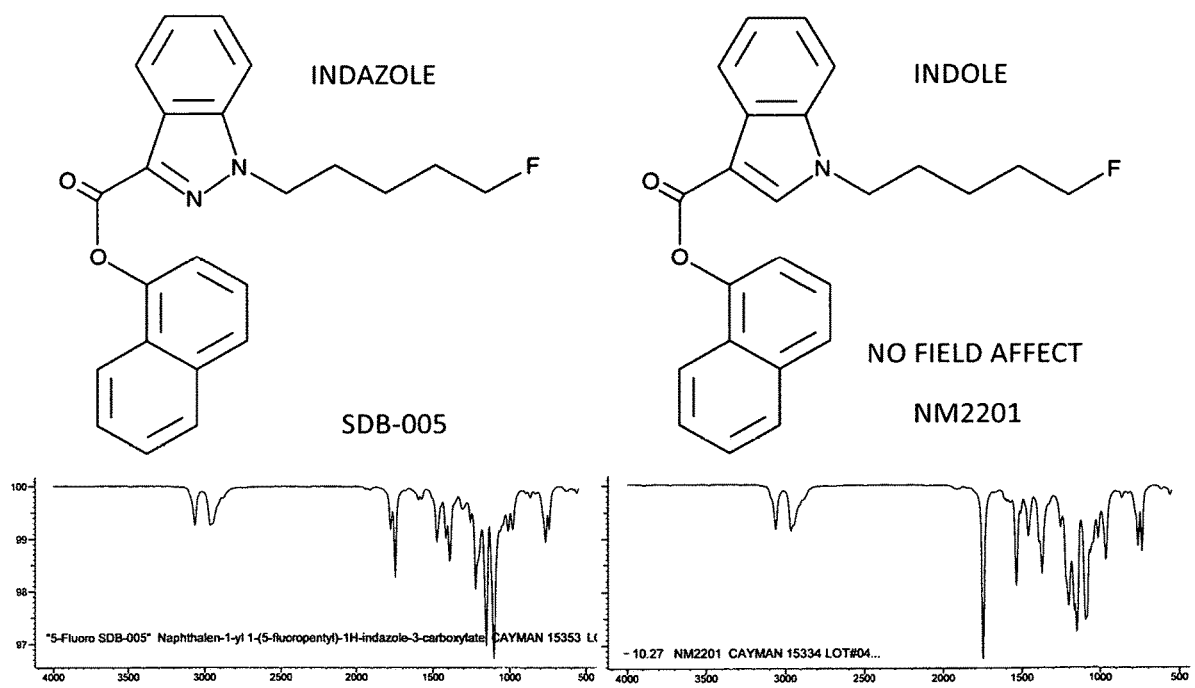
FIG. 4. illustrates two full scale infrared spectral plots of SDB-005 and NM2201 in the vapor phase. Further proof of the Field Effect can be found by comparing the carbonyl absorptions of these two similarly structured compounds in the 1750 wavenumber region. The only difference is the addition of one extra Nitrogen atom in the indazole ring of SDB-005 splitting the carbonyl absorption into two bands. The unshared electron pair from the Nitrogen atom on the indole ring of NM2201 is too far away to interact vicinal to the carbonyl during bond rotation.
Figure 5:
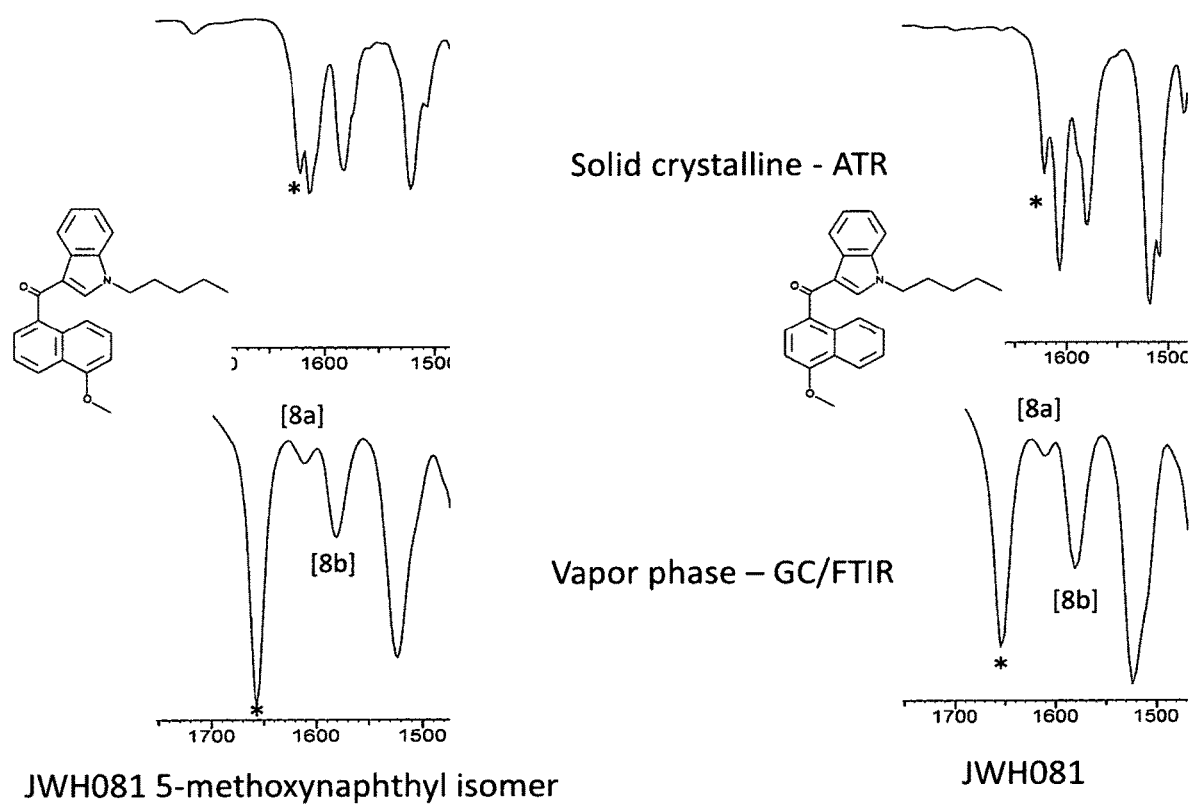
FIG. 5. illustrates overlaid infrared spectral plots of two JWHO81 positional isomers comparing crystalline solid phase in contrast to vapor phase. Vapor phase (bottom) significantly enhances the single carbonyl absorption for both isomers and shifts the band away from the Wilson 8a and 8b ring stretching bands.

Synthetic Cannabinoids represent the largest class of forensically encountered designer drugs. The BRIDGE TABLE represented in FIG. 1 provides a quick and accurate screening technique in order to properly identify 35 sub-categories within this class of drugs without the use of any initial standards. Since certain derivatives are Schedule I controlled dangerous substances, knowledge of the correct sub-class as a first step in the screening process is very important. An infrared spectrum of the unknown compound must be acquired in vapor phase at elevated temperatures between 250 to 290° C. by either a GC/FTIR system using light-pipe technology so that the column effluent remains in a vapor state or using a heated static vapor cell on a bench top FTIR system. All bands from the unknown spectrum between 1840-1640 cm$^{-1}$ are matched to the correct entry within the BRIDGE TABLE. From this, the molecular structure will be given in terms of the functional group making up the Bridge and its 2 adjoining pieces, one of which will always be a ring based system (core ring) which is present in all Synthetic Cannabinoids.

The BRIDGE TABLE is a result of an infrared relationship existing within the carbonyl cluster that can only be visualized in the vapor state and is capable of filtering the Synthetic Cannabinoids into 35 sub-categories. The values used in this table were based on real data. Vapor Phase Infrared Spectra of over 200 pure reference materials were acquired using standard GC/FTIR light-pipe technology at temperatures between 250 to 280° C. From this data, the Carbonyl Frequencies from these Synthetic Cannabinoids were systematically recorded and sorted according to their chemical structure. In order to classify all structures within this group into 35 separate sub-categories, the following scheme was used:

Synthetic Cannabinoids were classified according to the ring systems and functional groups present by defining each example into 3 basic pieces as designated in FIG. 6.
1. CORE RING SYSTEM (NUCLEOUS with the TAIL present)—Most common would be Indole and Indazole, but can also be other ring systems such as Benzimidazole, Pyrrole, and Carbazole
2. BRIDGE (A Single Functional Group) joining the Core Ring System with another Ring or Functional Group. Examples: Ketones, Esters, and Secondary Amides
3. SECONDARY RING SYSTEM such as Naphthalene, Benzene, Quinoline or another Functional Group such as an Ester or Primary Amide Not all Synthetic Cannabinoids possess a Secondary Ring System. In some classes, this ring system is replaced by a functional group. FIG. 6 illustrates both of these examples. One is a Naphthoylindole which has naphthalene Secondary Ring System with a methanone Bridge. In the case where no secondary ring system exists, the third piece is defined by the example of ADB-PINACA in FIG. 6. The dashed line in this example shows that the Bridge is defined as the complete functional group which is bonded to the core ring system (indazole) and is a secondary amide. The third piece (second functional group) begins where the dashed line separates the Bridge on the opposite side of the core ring system. In some cases it is a second functional group bonded to another ring system. No matter how complex the third piece is, its functional group moiety is always bonded to the Bridge functional group. These rules have been consistently applied to all derivatives examined and completely define all listed sub-categories in the table.

Certain sub-categories contain regulated controlled dangerous substances which can either be color coded in the Bridge Table or tagged in a digital software version. The following 12 sub-categories that contain controlled substances are listed in the format of the Bridge Table—BRIDGE FUNCTIONAL GROUP/CORE RING/SECONDARY RING OR FUNCTIONAL GROUP:
methanone/indole/naphthalene, methanone/indole/cyclopropane, methanone/indole/benzene, ethanone/indole/benzene, ester/indole/naphthalene, ester/indole/quinoline, secondary amide/indole/ester, secondary amide/indole/primary amide, secondary amide/indazole/adamantyl, secondary amide/indazole/ester, methanone/indazole/naphthalene, and secondary amide/indazole/1-methyl-phenylethyl The BRIDGE TABLE in FIG. 1 contains the following column headings:
BRIDGE CARBONYL FREQUENCY—This contains the entire Carbonyl Frequency range found for all 35 sub-categories of the Synthetic Cannabinoids. The actual range for each category never exceeded more than 4 wavenumbers. This is the pointer index and values from this column are used to compare Carbonyl value of an unknown compound as a first step.
BRIDGE FUNCTIONAL GROUP—List the type of functional groups responsible for joining the core ring and secondary ring system together: Methanone, Ethanone, Secondary Amide, or Ester.
ADDITIONAL CARBONYL FREQUENCY FROM PIECE—In some cases the Secondary Ring System is replaced with a Functional Group. If this group contains a Carbonyl moiety, the frequency is listed in this column.
UNIQUE CARBONYL FREQUENCY—A few special cases exist in which additional Carbonyl bands are found as a result of either the "Field Effect" from rotational isomerism or "Fermi Resonance".
ADJOINING PIECES—This column defines the other two ring systems and/or functional groups that are bonded to each side of the Bridge. Since the two occupy the same column, each are separated by a "/". When the proper match to all Carbonyl Frequencies are found, this information coupled with the Bridge Functional Group yields the complete sub-category molecular structure.

Starting from the bottom of the table and going up, the Carbonyl Bridge Frequencies are listed in ascending order. By comparing frequencies of unknown Synthetic Cannabinoids directly to this table, insights are quickly gained as to the correct Synthetic Cannabinoid Class. All sub-categories are identified by matching Bridge frequencies from unknown samples with the "BRIDGE C=O" carbonyl value. Additional Carbonyl bands from other functional groups are also listed in the table. This also includes unique carbonyl bands from rotational isomers and fermi resonance which also gives further clarification between the categories. All carbonyl absorptions are recorded from the unknown compound between 1840-1640 $cm^{-1}$ and noted. The carbonyl band cluster can contain one single band to a maximum of three bands. Only one category is found in the entire table that will yield three bands; these are examples that have a secondary amide Bridge bonded to a core ring of indole and a primary amide. The special bands listed in the "UNIQUE C=O" column are always the weakest bands in the cluster. A majority of sub-categories contain only one single carbonyl band with is easily assigned as the Bridge frequency. The last possibility arises when the unknown contains two bands within the region. In this case, the carbonyl band assigned as the Bridge frequency is the band which has the lower frequency of the two.

For instance, an unknown compound (JWH-018) yields a single carbonyl frequency of 1657 $cm^{-1}$. This frequency is matched to the first column "BRIDGE C=O" in the table with the range 1654-1657 yielding the class: METHANONE BRIDGE, INDOLE/NAPHTHALENE which represents a Methanone Bridge bonded to a Indole core ring and a Naphthalene secondary ring system.

Another unknown compound (PX-1) gives a three carbonyl bands within the cluster range. The weakest band of the three is at 1832 $cm^{-1}$ and is assigned as a UNIQUE C=O to the table. This leaves the other two bands at 1669 $cm^{-1}$ and 1723 $cm^{-1}$ to be assigned. The 1669 $cm^{-1}$ band is chosen as the Bridge Frequency since it is the lower of the two values. This value is now searched in the first column of the BRIDGE TABLE and falls within the range 1668-1671. The sub-category in this matching entry is Secondary Amide Bridge bonded to an Indole Core Ring and a Primary amide. The other two bands are identified as a Primary Amide Carbonyl band at 1723 cm$^{-1}$, and one unique Carbonyl band from fermi resonance at 1832 cm$^{-1}$.

A third unknown compound (AB-FUBINACA 3-fluorobenzyl isomer) is examined in vapor phase yielding two bands at 1688 cm$^{-1}$ and 1726 cm$^{-1}$. The lower frequency value of the two bands is 1688 cm$^{-1}$ and is chosen to be the Bridge Carbonyl. This value falls within the range of 1685-1688 cm$^{-1}$ listed in the Bridge Table. This entry also matches the second band as being an additional functional group within the range of 1725-1728 cm$^{-1}$. The sub-category listed for these values reflect that the unknown has a Secondary Amide Bridge (absorbing at 1688 cm$^{-1}$) bonded to and Indazole core ring and a Primary Amide (absorbing at 1726 cm$^{-1}$).

This invention provides a quick identity to the correct sub-category and legal status of an unknown Synthetic Cannabiniod without of a full search library or standard present for comparison. Choosing the bridge frequency in vapor phase as the first step in the presence of other carbonyl absorptions is a unique technique which can gain much insight to molecular structure from so few bands. No prior/current art exists for comparison and the history of vapor phase explains why this has never happened.

The invention claimed is:

1. A method of analyzing a suspected synthetic cannabinoid sample, comprising the steps of:
    Capturing the sample in a vapor state using either a heated static vapor cell on a benchtop FTIR spectrometer or flow cell from a GC/FTIR system at temperatures between 250-290 degrees Celsius;
    Directing infrared radiation from the infrared spectrometer through the captured vapor of the sample;
    Recording the resultant absorption spectrum across a frequency interval from a starting frequency of 1840 wavenumbers to an ending frequency of 1640 wavenumbers;
    Identifying between one and three carbonyl infrared absorption bands in the recorded resultant absorption spectrum;
    Identifying a bridge frequency within said between one and three carbonyl infrared absorption bands in the recorded resultant absorption spectrum;
    Matching each of said between one and three carbonyl infrared absorption bands to the best fitting match from reference data representing all synthetic cannabinoid categories, using the bridge frequency as the first band to compare; and
    Identifying the suspected synthetic cannabinoid sample based on said matching.

2. The method of claim 1, further comprising the steps of:
    Sequentially repeating the steps of claim 1;
    Generating an infrared carbonyl absorption frequency wavenumber table, based on data obtained from pure synthetic cannabinoid reference materials in the vapor state, and classifying them into three types of absorptions—the bridge frequency, carbonyl from secondary functional group, and unique rotational bands;
    Identifying the bridge frequency within each carbonyl band group which, if more than one band is present, is the band with the lowest frequency of the group;
    Sorting the tabulated data in the wavenumber table in order of increasing bridge frequency; and
    Linking said tabulated reference data directly to the overall molecular structure representing the synthetic cannabinoid category in terms of three basic pieces: the core ring, the bridge, and the secondary ring system or functional group.

3. A non-transitory, computer-readable medium containing instructions that, when executed by a computer, cause the method of claim 1 or claim 2 to be performed.

* * * * *